United States Patent [19]

Suda et al.

[11] Patent Number: 5,624,900
[45] Date of Patent: Apr. 29, 1997

[54] PEPTIDE OR ITS SALTS

[75] Inventors: Tatsuo Suda, Tachikawa; Etsuko Abe, Tokyo; Masao Tanihara; Chie Fujiwara, both of Kurashiki, all of Japan

[73] Assignee: Kuraray Co., Ltd., Kurashiki, Japan

[21] Appl. No.: 239,854

[22] Filed: May 9, 1994

Related U.S. Application Data

[63] Continuation of Ser. No. 752,426, Sep. 3, 1991, abandoned.

[30] Foreign Application Priority Data

Sep. 3, 1990 [JP] Japan ............................ 2-233571
Nov. 24, 1990 [JP] Japan ............................ 2-320000
Nov. 26, 1990 [JP] Japan ............................ 2-324956

[51] Int. Cl.$^6$ ............................ A61K 38/00; C07K 7/08; C07K 7/06
[52] U.S. Cl. ............................ 514/13; 514/16; 530/326; 530/328
[58] Field of Search ............................ 530/326, 328; 514/13–16

[56] References Cited

FOREIGN PATENT DOCUMENTS 0474141  3/1992  European Pat. Off. .

OTHER PUBLICATIONS

Eastgate, et al. Lancet, pp. 706–709, 1988.
Pompidon et al, Lancet p. 1423.
Tanihara et al, vol. 188, No. 2, Biochem and Biophysical Research Comm. pp. 912–920, 1992.
Nature, vol. 343, N. 6256, pp. 341–346, Jan. 25, 1990, S.P. Eisenberg, et al., "Primary Structure and Functional Expression from Complementary DNA of a Human Interleukin–1 Receptor Antagonist".

Chemical Abstracts, vol. 111, No. 23, p. 463, Dec. 4, 1989, 111:213060s, A. Tagliabue, et al., "Defining Agonist Peptides of Human Interleukin–1β".
Chemical Abstracts, vol. 109, No. 19, p. 143, Nov. 7, 1988, 109:164234z, S.H. Ferreira, et al., "Interleukin–1β as a Potent Hyperalgesic Agent Antagonized by a Tripeptide Analog".
Chemical Abstracts, vol. 109, No. 21, p. 545, Nov. 21, 1988, 109:188459c, T. Musso, et al., "Effect of a Synthetic Nonapeptide of Human IL–1β on the Cellular Immunoreactivity and In Vivo Growth of a Fibrosarcoma of BALB/c mice".
Chemical Abstracts, vol. 107, No. 21, p. 580, Nov. 23, 1987, 107:196195n, E.W. Palaszynski, "Synthetic C–Terminal Peptide of IL–1 Functions as a Binding Domain as well as an Antagonist for the IL–1 Receptor".

*Primary Examiner*—Cecilia Tsang
*Assistant Examiner*—S. G. Marshall
*Attorney, Agent, or Firm*—Oblon, Spivak, McClelland, Maier & Neustadt, P.C.

[57] ABSTRACT

Peptides having high binding activity for human interleukin-1 and represented by the following formula $$H\text{-}X^1\text{-}Cys\text{-}A\text{-}B\text{-}A\text{-}B\text{-}A\text{-}Ser\text{-}X^2\text{-}Y$$

wherein each A represents an amino acid residue selected from the group consisting of Val, Leu, Ile and Nle, independent of any other selection for A; B represents an amino acid residue selected from the group consisting of Arg, Lys, Gln, His and Ser, independent of any other selection for B; $X^1$ and $X^2$ each is a single bond or a peptide segment comprising 1–10 amino acid residues selected from Gly, Ala, Val, Arg, Asn, Ser, Phe, Pro, Leu, Glu, Asp, Lys, Thr, His, Tyr, Nle and Ile and Y represents a hydroxyl group or an amino group; and their salts.

9 Claims, No Drawings

PEPTIDE OR ITS SALTS

This application is a Continuation of application Ser. No. 07/752,426, filed on Sep. 3, 1991, now abandoned.

BACKGROUND OF THE INVENTION

1. Field of the Invention

The present invention relates to peptides or salts thereof having high binding activity for human interleukin-1 and a method of treating diseases resulting from abnormally high concentrations of interleukin-1 by administering to a patient in need of such treatment a pharmaceutically effective amount of such peptides.

2. Description of the Prior Art

Interleukin-1 (hereinafter referred to as "IL-1") is an important factor in the immune response and plays an important role in various inflammatory diseases.

It has been suggested that IL-1 participates in destruction of alveolar bone in periodontitis, bone resorption in osteoporosis and degradation of cartilage in rheumatoid arthritis. [See, for example, Interleukin 1, Protein, Nucleic Acid and Enzyme, [33] 10, 1728–1741 (1988).]

It has also been reported that an IL-1 inhibitor found in the supernatant of monocytes cultures is an antagonist of the IL-1 receptor, has a molecular weight of about 17,000 and inhibits various bioactivities of IL-1. [See, for example, W. P. Arend et al, J. Clin. Invest. 85, 1694–1697 (1990).]

This antagonist may be toxic to the liver, kidneys, or may display non-specific immunosuppression or similar harmful side effects.

It would be desirable to provide a peptide that exhibits IL-1-inhibiting activity, but does not bind to the IL-1 receptor.

SUMMARY OF THE INVENTION

It is an object of this invention to provide a peptide useful for the treatment of diseases precipitated by IL-1, such as rheumatoid arthritis or osteoporosis.

It is another object of the present invention to provide a method for treating diseases resulting from abnormally high concentrations of interleukin-1 by administering to a patient in need of such treatment a pharmaceutically effect amount of such peptides.

These and other objects which will become apparent during the following descriptions have been achieved by peptides having high binding activity for human interleukin-1 and represented by the following formula (I)

$\text{H-}X^1\text{-Cys-A-B-A-B-A-Ser-}X^2\text{-Y}$   (I)

wherein A represents an amino acid residue selected from the group consisting of Val, Leu, Ile and Nle, independent of any other selection for A; B represents an amino acid residue selected from the group consisting of Arg, Lys, Gln, His and Ser, independent of any other selection for B; $X^1$ and $X^2$ each is a single bond or a peptide segment comprising 1–10 amino acid residues selected from Gly, Ala, Val, Arg, Asn, Ser, Phe, Pro, Leu, Glu, Asp, Lys, Thr, His, Tyr, Nle and Ile; and Y represents a hydroxyl group or an amino group; or salts thereof.

This object as well as other objects and advantages of the present invention will become apparent to those skilled in the art from the following detailed description.

DESCRIPTION OF THE PREFERRED EMBODIMENTS

In this specification, various amino acid residues are expressed in the following abbreviations.

Ala: L-alanine residue
Arg: L-arginine residue
Asn: L-asparagine residue
Cys: L-cysteine residue
Gln: L-glutamine residue
Glu: L-glutamic acid residue
Gly: Glycine residue
His: L-histidine residue
Ile: L-isoleucine residue
Leu: L-leucine residue
Lys: L-lysine residue
Phe: L-phenylalanine residue
Pro: L-proline residue
Ser: L-serine residue
Thr: L-threonine residue
Trp: L-tryptophan residue
Tyr: L-tyrosine residue
Val: L-valine residue
Nle: L-norleucine residue This specification employs the common practice of expressing an amino acid sequence of peptides, i.e. placing an N-terminal amino acid residue at the left side of the sequence and a C-terminus at the right side.

Among the peptides represented by the above formula (I), those represented by the following formula (II) are preferred.

$\text{H-}X^3\text{-D-}X^4\text{-Y}$   (II)

wherein D represents a peptide segment represented by -Cys-Leu-Arg-Ile-Lys-Ile-Ser-(SEQ ID NO:2), one represented by -Cys-Leu-Gln-Ile-Lys-Ile-Ser-(SEQ ID NO:2) or one represented by -Cys-Leu-Gln-Ile-Gln-Ile-Ser-(SEQ ID. NO:3); $X^3$ and $X^4$ each represents a single bond or a peptide segment comprising 1 to 10 amino acid residues selected from Gly, Ala, Val, Arg, Asn, Ser, Phe, Pro, Leu, Glu, Asp, Lys, Thr, His, Tyr and Ile; and Y represents a hydroxyl group or an amino group or salts thereof.

Representative examples of the peptides provided by the present invention are as follows.

(a) H-Val-Val-Arg-Asn-Ser-Ser-Tyr-Cys-Leu-Arg-Ile-Lys-Ile-Ser-Ala-Lys-OH(SEQ ID NO:4), (b) H-Lys-Asn-Ser-Ser-Tyr-Cys-Leu-Arg-Ile-Lys-Ile-Ser-Ala-Lys-Phe-Val-Glu-OH(SEQ ID NO:5), (c) H-Lys-Tyr-Cys-Leu-Arg-Ile-Lys-Ile-Ser-Ala-Lys-Phe-Val-Glu-Asn-Glu-Pro-OH (SEQ ID NO:6), (d) H-Tyr-Cys-Leu-Arg-Ile-Lys-Ile-Ser-Ala-Lys-OH (SEQ ID NO:7), (e) H-Tyr-Cys-Leu-Arg-Ile-Lys-Ile-Ser-OH (SEQ ID NO:8), (f) H-Cys-Leu-Arg-Ile-Lys-Ile-Ser-OH (SEQ ID NO:1), (g) H-Lys-Cys-Leu-Arg-Ile-Lys-Ile-Ser-OH (SEQ ID NO:9), (h) H-Cys-Leu-Gln-Ile-Lys-Ile-Ser-OH (SEQ ID NO:2), (i) H-Lys-Cys-Leu-Gln-Ile-Gln-Ile-Ser-OH (SEQ. ID. NO. 10)

(j) H-Lys-Ile-Cys-Ile-Arg-Ile-Gln-Ile-Ser-OH (SEQ ID. NO. 11), (k) H-Lys-Nle-Cys-Nle-Arg-Nle-Gln-Nle-Ser-OH (SEQ ID. NO:12), (l) H-Lys-Ile-Cys-Ile-His-Ile-Gln-Ile-Ser-OH (SEQ ID. NO:13), (m) H-Lys-Ile-Cys-Leu-Arg-Ile-Gln-Ile-Ser-OH,(SEQ ID. NO:14), (n) H-Lys-Cys-Val-Gln-Val-Gln-Val-Ser-OH (SEQ ID. NO:15) and (o) H-Lys-Ile-Cys-Ile-Arg-Ile-Gln-Ile-Ser-$NH_2$ (SEQ ID NO:16).

The salts of the peptides of the present invention are those physiologically acceptable and examples are salts with an acid, such as hydrochloric acid, sulfuric acid, phosphoric acid, lactic acid, tartaric acid, maleic acid, fumaric acid, oxalic acid, malic acid, citric acid, oleic acid or palmitic acid, salts with a hydroxide or carbonate of an alkali metal, alkali earth metal, or other metals, such as sodium, potassium, calcium or aluminum, and salts with triethylamine, benzylamine, diethanolamine, t-butylamine, dicyclohexylamine, arginine and the like.

The peptides of the present invention can be produced by known processes, e.g. solid phase synthesis and liquid phase synthesis, among which solid phase synthesis is preferred because of its simple and easy operation. See for example Zoku Seikagaku Jikken Koza 2, Tanpakushitsu No Kagaku (Ge) {Biochemistry Experiments Course 2, Second Series; Chemistry of Protein (the latter half} edited by Japan Biochemical Society, published on May 20, 1987 by Tokyo Kagaku Dojin Co., Ltd., pages 641–694.

The steps for producing the peptides of the present invention by a solid phase synthesis are described below.

The amino acid corresponding to the C-terminus of the desired peptide is bonded via its α-COOH group to a polymer insoluble in the reaction solvent to be used, such as styrene-divinylbenzene copolymer. The amino acid is then bonded by condensation, toward in the direction of the N-terminus of the desired peptide, to the next corresponding amino acid or peptide segment, with its functional groups such as α-amino group other than its α-COOH group having previously been protected. Next, the protecting groups possessed by the peptide-forming α-amino group and the like of the thus bonded amino acid or peptide segment are removed. The above steps of condensation and removal of protecting group are successively repeated to extend the peptide chain to eventually obtain the peptide chain corresponding to the desired peptide. The thus formed peptide chain is separated from the polymer and the remaining protecting groups are removed from the protected functional groups, to obtain the desired peptide, which is then purified. Here, the separation of the peptide chain from the polymer and the removal of the protecting groups are preferably conducted at the same time using hydrogen fluoride for the purpose of suppressing occurrence of side reactions. The purification of the obtained peptide is effectively conducted by reversed phase high performance liquid chromatography.

The salts of the peptides of the present invention are prepared by known salt formation reactions.

The peptides and their salts (hereinafter simply referred to as "peptides") of the present invention have a specific binding activity for human IL-1 and can hence inhibit the activity of IL-1 without binding to the IL-1 receptor.

Toxicity tests have confirmed that the peptides of the present invention are of low toxicity.

The peptides of the present invention therefore are effective for treating diseases caused by excess production IL-1, such as rheumatoid arthritis and osteoporosis.

Once administered to patients suffering from a disease such as rheumatoid arthritis or osteoporosis, the peptides of the present invention can relieve the conditions of the patients because they bind and neutralize the IL-1 in their blood serum and synovia.

The dosage to manifest an effective activity of the peptides of the present invention is generally 0.01 μg/kg to 2 g/kg (adult), preferably 0.01 μg/kg to 200 mg/kg (adult).

It is desirable to administer the peptide in the form of a solution obtained by dissolving it in a physiologically acceptable solution such as saline or an 5% aqueous solution of glucose. The peptide solution may contain various additives which are pharmacologically acceptable.

The peptide solution can be administered intravenously, subcutaneously, intraperitoneally, intraarticularly or by like methods. The peptide can also be administered orally in the form of a capsule or liposome.

EXAMPLES

Other features of the invention will become apparent in the course of the following descriptions of exemplary embodiments which are given for illustration of the invention and are not intended to be limiting thereof.

Example 1

A peptide represented by the formula H-Val-Val-Arg-Asn-Ser-Ser-Tyr-Cys-Leu-Arg-Ile-Lys-Ile-Ser-Ala-Lys-OH (SEQ ID NO:4) is prepared by solid phase synthesis with an automatic peptide synthesizer.

That is, 0.1 mmole of a granular resin comprising a styrene-divinylbenzene copolymer (molar ratio of styrene to and divinyl benzene: 99:1) containing 0.65 mmole/g-resin of 4-[$N^\alpha$-(t-butoxycarbonyl)-$N^\epsilon$-(p-chlorobenzyloxycarbonyl-L-lypyloxymethyl]-phenylacetamidemethyl group [PAM lysine, t-Boc-L-Lys (C1-Z) made by Applied Biosystems Inc., U.S.A.] was used for binding successively the corresponding amino acids thereto in order in the direction of the N-terminal of the desired peptide. The amino acids used in the binding reactions were, all made by Applied Biosystems Inc., U.S.A, $N^\alpha$-(t-butoxycarbonyl)-$N^\epsilon$-(p-chlorobenzyloxycarbonyl)-L-lysine (t-Boc lysine), N-(t-butoxycarbonyl)-L-leucine (t-Boc leucine), N-(t-butoxycarbonyl)-O-(2-bromobenzyloxycarbonyl)-L-tyrosine (t-Boc tyrosine), N-(t-butoxycarbonyl)-L-isoleucine (t-Boc isoleucine), N-(t-butoxycarbonyl)-L-asparagine (t-Boc asparagine), N-(t-butoxycarbonyl)-O-benzyl-L-serine (t-Boc serine), N-(t-butoxycarbonyl)-S-(p-methoxybenzyl)-L-valine (t-Boc valine), $N^\alpha$-(t-butoxycarbonyl) -$N^G$-(mesitylene-2-sulfonyl)-N-arginine (t-Boc arginine) and N-(t-butoxycarbonyl)-L-alanine (t-Boc alanine) each in an amount of 1 mmole.

The peptide thus obtained was subjected to removal of protecting groups and separation from the solid phase with a reaction apparatus (HF Reaction Apparatus Type I, made by Peptide Kenkyusho Co., Ltd.). The crude product was purified with a preparative reverse phase high performance liquid chromatograph manufactured by Milipore Waters Co. (column: Delta Pack C-18, 47×300 mm, attached with a pressing module of Prep Pack 1,000). The purified peptide was tested by analytical reverse phase high performance liquid chromatography {LC6A, made by Shimadzu Corporation; column: TSK gel ODS-80TM CTR, mobile phase: mixed solvent of acetonitrile containing 0.05% by volume of trifluoroacetic acid and water (the concentration of acetonitrile was gradually changed from 5% by volume to 50% by volume over 30 minutes)}, and the result showed a single peak at 17.1 minutes. FAB mass spectrometry revealed that the purified peptide had a molecular weight of 1,838 (theoretical value: 1837.2).

Examples 2 through 15 and Comparative Example

The procedure of Example 1 was followed to synthesize peptides represented by the formulas H-Lys-Asn-Ser-Ser-Tyr-Cys-Leu-Arg-Ile-Lys-Ile-Ser-Ala-Lys-Phe-Val-Glu-OH (Example 2 SEQ ID NO:5), H-Lys-Tyr-Cys-Leu-Arg-Ile-Lys-Ile-Ser-Ala-Lys-Phe-Val-Glu-Asn-Glu-Pro-OH (Example 3 SEQ ID NO:6), H-Tyr-Cys-Leu-Arg-Ile-Lys- Ile-Ser-Ala-Lys-OH (Example 4 SEQ ID NO:7), H-Tyr-Cys-Leu-Arg-Ile-Lys-Ile-Ser-OH (Example 5 SEQ ID NO:8), H-Cys-Leu-Arg-Ile-Lys-Ile-Ser-OH (Example 6 SEQ ID NO:1), H-Lys-Cys-Leu-Arg-Ile-Lys-Ile-Ser-OH (Example 7 SEQ ID NO:9), H-Cys-Leu-Gln-Ile-Lys-Ile-Ser-OH (Example 8 SEQ ID NO:2), H-Lys-Cys-Leu-Gln-Ile-Gln-Ile-Ser-OH (Example 9 SEQ ID NO:10), H-Lys-Ile-Cys-Ile-Arg-Ile-Gln-Ile-Ser-OH (Example 10 SEQ ID NO:11), H-Lys-Nle-Cys-Nle-Arg-Nle-Gln-Nle-Ser-OH (Example 11 SEQ ID NO:10), H-Lys-Ile-Cys-Ile-His-Ile-Gln-Ile-Ser-OH (Example 12 SEQ ID NO:13), H-Lys-Ile-Cys-Ile-Leu-Arg-Ile-Gln-Ile-Ser-OH (Example 13 SEQ ID NO:14), H-Lys-Cys-Val-Gln-Val-Gln-Val-Ser-OH (Example 14 SEQ ID NO:15), H-Lys-Ile-Cys-Ile-Arg-Ile-Gln-Ile-Ser-NH$_2$ (Example 15 SEQ ID NO:16) and H-Tyr-Ser-Leu-Glu-Ile-Lys-Ile-Ser-OH (Comparative Example SEQ ID NO:17).

In Example 2, 0.1 mmole of a granular resin comprising a styrene-divinylbenzene copolymer (molar ratio of styrene to divinyl benzene: 99:1) containing 0.70 mmole/g-resin of 4-[N-(t-butoxycarbonyl)-γ-benzyl-L-glutamyloxymethyl]-phenylacetamidomethyl group [PAM Glutamic acid, t-Boc-L-GLu (OBzl) made by Applied Biosystems Inc., U.S.A.] was used; in Example 3, 0.1 mmole of a granular resin comprising a styrene-divinylbenzene copolymer (molar ratio of styrene to divinyl benzene: 99:1) containing 0.78 mmole/g-resin of 4-[N-(t-butoxycarbonyl)-L-prolyloxymethyl]-phenylacetamidomethyl group (PAM proline, t-Boc-L-Pro, made by Applied Biosystems Inc., U.S.A..); in Example 4, 0.1 mmole of a granular resin comprising a styrene-divinylbenzene copolymer (molar ratio of styrene to divinyl benzene: 99:1) containing 0.65 mmole/g-resin of 4-[N$^\alpha$-(t-butoxycarbonyl)-N$^\epsilon$-(p-chlorobenzyloxycarbonyl)-L-lysyloxymethyl]-phenylacetamidomethyl group [PAM lysine, t-Boc-L-Lys (Cl-Z), made by Applied Biosystems Inc., U.S.A.]; in Examples 5 through 14 and Comparative Example, 0.1 mmole of a granular resin comprising a styrene-divinylbenzene copolymer (molar ratio of styrene to divinyl benzene: 99:1) containing 0.72 mmole/g-resin of 4-[N-(t-butoxycarbonyl)-O-benzyl-L-seryloxymethyl]-phenylacetamidomethyl group [PAM serine, t-Boc-L-Ser (Bzl) made by Applied Biosystems Inc., U.S.A.] was used; and in Example 15, 0.1 mmole of a granular resin comprising a styrene-divinylbenzene copolymer (molar ratio of styrene to divinyl benzene: 99:1) containing 0.78 mmole/g-resin of α-amino-p-methylbenzyl (p-methyl BHA resin, made by Applied Biosystems Inc., U.S.A.).

The amino acids used in addition to those in Example 1 are, all made by Applied Biosystems Inc. U.S.A., N-(t-butoxycarbonyl)-L-phenylalanine (t-Boc phenylalanine), N-(t-butoxycarbonyl)-γ-benzyl-L-glutamic acid (t-Boc glutamic acid), N-(t-butoxycarbonyl)-L-glutamine (t-Boc glutamine), N-(t-butoxycarbonyl)-L-norleucine (t-Boc norleucine) and N-(t-butoxycarbonyl)-N$^{Im}$-(2,4-dinitrophenyl)-L-histidine (t-Boc histidine).

The peptides thus obtained were subjected to removal of protecting groups and separation from the solid phase, in the same manner as in Example 1, to give crude products, which were then purified in the same manner. The purified peptides were tested by analytical high performance liquid chromatography and their molecular weights analyzed by FAB mass spectrometry. The results are summarized in Table 1.

TABLE 1

| Example | Elution time | Molecular weight Observed | Molecular weight Theoretical |
| --- | --- | --- | --- |
| Example 2 | 19.6 min | 1986 | 1986.33 |
| Example 3 | 19.5 min | 2038 | 2038.41 |
| Example 4 | 17.3 min | 1194 | 1194.49 |
| Example 5 | 18.5 min | 995 | 995.24 |
| Example 6 | 16.6 min | 833 | 832.07 |
| Example 7 | 15.5 min | 963 | 960.24 |
| Example 8 | 17.6 min | 805 | 804.1 |
| Example 9 | 17.2 min | 933 | 932.14 |
| Example 10 | 19.7 min | 1073 | 1073.35 |
| Example 11 | 20.0 min | 1073 | 1073.35 |
| Example 12 | 18.9 min | 1054 | 1054.31 |
| Example 13 | 19.0 min | 1074 | 1073.35 |
| Example 14 | 12.6 min | 890 | 890.06 |
| Example 15 | 18.8 min | 1072 | 1072.37 |
| Comparative Example | 19.2 min | 953 | 952.1 |

Example 16

Binding Activity for Human IL-1

Adsorbents each having fixed 1 mg of one of the peptides obtained in Examples 1 through 15 and the Comparative Example were prepared as follows. One gram of a granular cellulose (CM-CELLULOFINE CH, available from Seikagaku Kogyo Co., Ltd.) is suspended in 5 ml of dioxane purified by distillation in the presence of sodium metal. To the suspension thus obtained was added 0.05 g of N-hydroxysuccinimide and 0.1 g of dicyclohexylcarbodimide, and the mixture was shaken at a room temperature for 1 night. The mixture thus obtained was washed with a 0.02 mole/l phosphate buffer (pH: 7.4) and then filtered with suction. The granules thus obtained were mixed with 1 ml of 0.02 mol/l phosphate buffer or purified water containing 1 mg of each one of the peptides obtained in Examples 1 through 15 and the Comparative Example. The mixtures were shaken overnight at a temperature of 4° C. and filtered with suction. The filtrates were tested by analytical reverse phase high performance liquid chromatography and none of them showed any remaining unreacted peptides.

From the thus prepared adsorbents, 100 mg each was weighed, and thereto was added 100 μl of 5% solution of bovine serum albumin in PBS (a 10 mM phosphate buffer solution containing 0.15M NaCl, pH: 7.4). The mixtures were incubated overnight at 4° C., then about 300 Bq of $^{125}$I-labelled human IL-1β (purchased from Amersham Japan) was added to them and the mixtures were incubated at a room temperature for 3 hours. The reaction mixtures thus obtained were washed 5 times with Tris buffer containing 0.2% of Triton X-100 and then tested for radioactivity remaining on the adsorbents with a γ counter. The results are shown in Table 2.

TABLE 2

| Adsorbent | Radioactivity (cpm) |
| --- | --- |
| Example 1 | 922 |
| Example 2 | 764 |
| Example 3 | 1171 |
| Example 4 | 891 |
| Example 5 | 840 |
| Example 6 | 815 |
| Example 7 | 576 |
| Example 8 | 678 |

TABLE 2-continued

| Adsorbent | Radioactivity (cpm) |
|---|---|
| Example 9 | 1100 |
| Example 10 | 1373 |
| Example 11 | 1292 |
| Example 12 | 1167 |
| Example 13 | 1245 |
| Example 14 | 890 |
| Example 15 | 1427 |
| Comparative Example | 84 |
| Reference Example | 45 |

As shown in Table 2, the adsorbents having immobilized thereon the peptides obtained in Examples 1 through 15 have significantly higher radioactivities than those having immobilized thereon the peptide obtained in Comparative Example and glycine (H-Gly-OH) (Reference Example), thus proving their high binding activity for human IL-1.

Obviously, numerous modifications and variations of the present invention are possible in light of the above teachings. It is therefore to be understood that within the scope of the appended claims, the invention may be practiced otherwise than as specifically described herein.

---

What is claimed is:

1. A peptide having high binding activity for human interleukin-1 and having the formula:

$$H\text{-}X^1\text{-}Cys\text{-}A\text{-}B\text{-}A\text{-}B\text{-}A\text{-}Ser\text{-}X^2\text{-}Y$$

wherein A represents an amino acid residue selected from the group consisting of Val, Leu, Ile and Nle, independent of any other selections for A; each B represents an amino acid residue selected from the group consisting of Arg, Lys, Gln, His and Ser, independent of any other selections for B; $X^1$ and $X^2$ is each a single bond; and Y represents a hydroxyl or amino group; or a salt thereof.

2. The peptide of claim 1, which is selected from the group consisting of:

H-Cys-Leu-Arg-Ile-Lys-Ile-Ser-OH (Seq ID NO:1), and

H-Cys-Leu-Gln-Ile-Lys-Ile-Ser-OH (Seq ID NO:2).

3. A pharmaceutical composition, comprising:

a) one or more peptides having high binding activity for human interleukin-1 and having the formula:

$$H\text{-}X^1\text{-}Cys\text{-}A\text{-}B\text{-}A\text{-}B\text{-}A\text{-}Ser\text{-}X^2\text{-}Y$$

wherein A represents an amino acid residue selected from the group consisting of Val, Leu, Ile and Nle, independent of any other selections for A; each B represents an amino acid residue selected from the group consisting of Arg, Lys, Gln, His and Ser, independent of any other selections for B; $X^1$ and $X^2$ is each a single bond; and Y represents a hydroxyl or amino group; or a salt thereof; and b) a pharmaceutically acceptable carrier.

4. The pharmaceutical composition of claim 3, wherein said one or more peptides are selected from the group consisting of:

H-Cys-Leu-Arg-Ile-Lys-Ile-Ser-OH (Seq ID NO:1), and

H-Cys-Leu-Gln-Ile-Lys-Ile-Ser-OH (Seq ID NO:2).

5. The pharmaceutical composition of claim 3, which is in a form of a saline solution.

6. The pharmaceutical composition of claim 3, which is in a form of a 5% aqueous solution of glucose.

7. The pharmaceutical composition of claim 3, which is in a form of capsules or liposomes.

8. A method of treating rheumatoid arthritis resulting from abnormally high concentrations of interleukin-1, comprising administering to a patient in need thereof a pharmaceutically effective amount of a peptide having a formula:

$$H\text{-}X^1\text{-}Cys\text{-}A\text{-}B\text{-}A\text{-}B\text{-}A\text{-}Ser\text{-}X^2\text{-}Y$$

wherein each A represents an amino acid residue selected from the group consisting of Val, Leu, Ile and Nle, independent of any other selections for A; each B represents an amino acid residue selected from the group consisting of Arg, Lys, Gln, His and Ser, independent of any other selections for B; $X^1$ and $X^2$ is each a single bond; and Y represents a hydroxyl or amino group; or a salt thereof.

9. The method of claim 8, wherein said peptide is selected from the group consisting of:

H-Cys-Leu-Arg-Ile-Lys-Ile-Ser-OH (Seq ID NO:1), and

H-Cys-Leu-Gln-Ile-Lys-Ile-Ser-OH (Seq ID NO:2).

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Cys  Leu  Arg  Ile  Lys  Ile  Ser
    1                      5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Cys  Leu  Gln  Ile  Lys  Ile  Ser
    1                      5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Cys  Leu  Gln  Ile  Gln  Ile  Ser
    1                      5

( 2 ) INFORMATION FOR SEQ ID NO:4:

( i ) SEQUENCE CHARACTERISTICS:
        ( A ) LENGTH: 16 amino acids
        ( B ) TYPE: amino acid (D) TOPOLOGY: linear (ii) MOLECULE TYPE: peptide (xi) SEQUENCE DESCRIPTION: SEQ ID NO:4:

```
Val  Val  Arg  Asn  Ser  Ser  Tyr  Cys  Leu  Arg  Ile  Lys  Ile  Ser  Ala  Lys
1                 5                        10                       15
```

(2) INFORMATION FOR SEQ ID NO:5:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:5:

```
Lys  Asn  Ser  Ser  Tyr  Cys  Leu  Arg  Ile  Lys  Ile  Ser  Ala  Lys  Phe  Val
1                 5                        10                       15

Glu
```

(2) INFORMATION FOR SEQ ID NO:6:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:6:

```
Lys  Tyr  Cys  Leu  Arg  Ile  Lys  Ile  Ser  Ala  Lys  Phe  Val  Glu  Asn  Glu
1                 5                        10                       15

Pro
```

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:7:

```
Tyr  Cys  Leu  Arg  Ile  Lys  Ile  Ser  Ala  Lys
1                 5                        10
```

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:8:

```
Tyr  Cys  Leu  Arg  Ile  Lys  Ile  Ser
1                 5
```

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (i i) MOLECULE TYPE: protein (x i) SEQUENCE DESCRIPTION: SEQ ID NO:9:

```
Lys Cys Leu Arg Ile Lys Ile Ser
1               5
```

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (x i) SEQUENCE DESCRIPTION: SEQ ID NO:10:

```
Lys Cys Leu Gln Ile Gln Ile Ser
1               5
```

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:11:

```
Lys Ile Cys Ile Arg Ile Gln Ile Ser
1               5
```

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:12:

```
Lys Xaa Cys Xaa Arg Xaa Gln Xaa Ser
1               5
```

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:13:

```
Lys Ile Cys Ile His Ile Gln Ile Ser
1               5
```

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:14:

```
    Lys   Ile   Cys   Leu   Arg   Ile   Gln   Ile   Ser
     1                       5
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
    Lys   Cys   Val   Gln   Val   Gln   Val   Ser
     1                       5
```

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
    Lys   Ile   Cys   Ile   Arg   Ile   Gln   Ile   Ser
     1                       5
```